United States Patent
May (10) Patent No.: US 9,494,556 B2
(45) Date of Patent: Nov. 15, 2016

(54) ACTIVE MECHANICAL FORCE AND AXIAL LOAD SENSOR

(71) Applicant: PolyResearch AG, Chur (CH)

(72) Inventor: Lutz May, Berg (DE)

(73) Assignee: POLYRESEARCH AG, Chur (CH)

( * ) Notice: Subject to any disclaimer, the term of this patent is extended or adjusted under 35 U.S.C. 154(b) by 431 days.

(21) Appl. No.: 13/738,618

(22) Filed: Jan. 10, 2013

(65) Prior Publication Data

US 2013/0181702 A1    Jul. 18, 2013

(30) Foreign Application Priority Data

Jan. 13, 2012  (EP) .................................... 12151163
Dec. 7, 2012   (EP) .................................... 12196164
Dec. 14, 2012  (EP) .................................... 12197273

(51) Int. Cl.

| | |
|---|---|
| *G01B 7/16* | (2006.01) |
| *G01L 1/00* | (2006.01) |
| *G01N 27/72* | (2006.01) |
| *G01D 5/14* | (2006.01) |
| *G01L 1/12* | (2006.01) |
| *G01L 3/10* | (2006.01) |

(52) U.S. Cl.
CPC .............. *G01N 27/72* (2013.01); *G01D 5/145* (2013.01); *G01L 1/12* (2013.01); *G01L 1/127* (2013.01); *G01L 3/101* (2013.01)

(58) Field of Classification Search
CPC ............................... G01N 27/72; G01N 27/725
USPC .................................... 324/209, 243; 73/779
See application file for complete search history.

(56) References Cited

U.S. PATENT DOCUMENTS

| | | | |
|---|---|---|---|
| 4,523,482 A | * | 6/1985 | Barkhoudarian ........ 73/862.336 |
| 4,803,885 A |   | 2/1989 | Nonomura et al. |
| 2011/0199081 A1 | * | 8/2011 | Masuda ............... G01N 27/725 |
| | | | 324/258 |

FOREIGN PATENT DOCUMENTS

| | | | |
|---|---|---|---|
| JP | WO 2004094939 A1 * | 11/2004 | ............. G01N 27/72 |
| WO | 01/79801 | 10/2001 | |
| WO | 02/23146 | 3/2002 | |

(Continued)

OTHER PUBLICATIONS

Author: B. Zhu, M. J. Johnson, C. C. H. Lo, and D. C. Jiles, Title: Multifunctional Magnetic Barkhausen Emission Measurement System, Date: May 2001, Publication: IEEE Transactions of Magnetics, vol. 37, No. 3, pp. 1095-1099.*

*Primary Examiner* — Lisa Caputo
*Assistant Examiner* — Roger Hernandez-Prewit
(74) *Attorney, Agent, or Firm* — Fay Kaplun & Marcin, LLP (57) ABSTRACT

A force measurement sensor for measuring an applied force onto an object is provided. The force measurement sensor includes a sensing unit including a concentrator, a generator, a detector, and an evaluator. The concentrator points towards the object. The generator generates a magnetic field. The detector detects a magnetic field generated by the generator and influenced by the applied force to be measured. The detector outputs a first signal of the detected magnetic field. The evaluator evaluates a signal strength of the signal and determines the applied force based on the signal. A longitudinal axis of the detector is arranged for a lateral offset between the longitudinal axis of the detector and a central axis of the concentrator that is perpendicular to a longitudinal direction of the concentrator.

18 Claims, 7 Drawing Sheets

(56) References Cited

FOREIGN PATENT DOCUMENTS

WO    WO 2010050155 A1 * 5/2010 ............. G01N 27/80

* cited by examiner

ACTIVE MECHANICAL FORCE AND AXIAL LOAD SENSOR

FIELD OF THE INVENTION

The present invention relates to a contactless force measurement sensor and to a sensing arrangement having such a contactless force measurement sensor for measuring an applied force onto an object, in particular an axial force applied to a longitudinal object.

TECHNICAL BACKGROUND

Force measurement is important for many industrial applications, in particular for arrangements being dynamically impacted by a force. Applied forces may be pressuring forces as well as moments like torque, bending impact, or forces in an axial direction of an object. An exemplary application for torque is a shaft for a vehicle being arranged between a motor and e.g. a wheel. For determining a force in the shaft, either a particular element may need to be mounted to the shaft, or the shaft may need to be pre-processed, e.g. magnetized. Mounting elements to a shaft may influence the movement of the shaft, pre-processing may be difficult when the shaft is not accessible or cannot be dismounted for pre-processing.

In industrial applications and laboratory research and development applications, strain gauge sensors are used to measure bending forces. There are only a few other alternative sensor solutions available that may provide adequate bending sensor performance and are suitable for environmental conditions typical for the automotive, industrial, and consumer market.

SUMMARY OF THE INVENTION

The present invention relates to a force measurement sensor and in particular a contactless force measurement sensor for measuring an axial force in a longitudinal object.

According to an aspect of the invention, a force measurement sensor for measuring an applied force onto an object is provided. The force measurement sensor comprises a first sensing unit which comprises a first flux concentrator having a first facing orientation pointing towards a surface of the object, a first magnetic field generating unit being adapted for generating a magnetic field, a first magnetic field detector unit being adapted for detecting a first magnetic field which field being generated by the first magnetic field generating unit and being influenced by the applied force to be measured, wherein the first magnetic field detector unit is further adapted for outputting a first signal being representative for the detected magnetic field, and an evaluating unit being adapted for evaluating a signal strength of the first signal and determining the applied force based on the first signal. A longitudinal axis of the first magnetic field detector unit is arranged such that a first lateral offset between the longitudinal axis of the first magnetic field detector unit and a central axis of the first flux concentrator is provided. The first lateral offset is perpendicular to a longitudinal direction of the first flux concentrator.

The force measurement sensor may in particular be a contactless force measurement sensor adapted to measure in particular an axial load to a longitudinal object, i.e. a tensile force or a compressive force each having at least one force component in longitudinal direction of the object or parallel to the longitudinal direction of the flux concentrator.

Active magnetic principle mechanical force sensor means that there will be no need for a "permanent" magnetization of the object to be sensed to make the sensor work. A force sensor can function immediately after placing the sensor hardware appropriately close to the test object or object to be sensed.

The force measurement sensor may not need to be physically attached to the object to be sensed. There can be a gap of a few millimeters between the sensor and the object to be sensed and it will still work. Therefore this sensor works whatever the object to be sensed surface may be (coated, painted, dusty, for example), which may be ideal for measuring on construction sites, bridges, cranes, building frame works.

The force measurement sensor works with any metallic material or object to be sensed material containing metallic material as long as the magnetic properties of the material are sufficient to attract and/or hold a permanent magnet. This may apply to only a limited degree or substantially not to sintered materials as they may be too brittle when bending forces are applied.

In other words, the first magnetic field generating unit generates a magnetic field whose field lines spread towards the object to be sensed. The first magnetic field detector unit detects the magnetic field lines and in particular the spread, distracted, or diverged magnetic field lines, wherein the spreading and diverging of the magnetic field lines is influenced by a force applied to the object to be sensed such that the current induced to the first magnetic field detector unit varies dependent on the spread, distracted, and diverged magnetic field lines.

The lateral offset may be perpendicular to the facing orientation and the longitudinal direction of the flux concentrator, wherein the facing orientation may be perpendicular to the surface of the object. In one embodiment, the lateral offset may be arranged orthogonally with respect to a plane defined by the facing orientation and the longitudinal direction of the flux concentrator.

The lateral offset is a lateral displacement greater than 0 mm between the longitudinal direction or longitudinal line of symmetry of the flux concentrator and the first magnetic field detector unit and may be a few mm or fractions of 1 mm. In one embodiment, there may be no lateral offset.

The force measurement sensor as described above and hereinafter is about a magnetic principle mechanical force sensor design that can detect and quantify mechanical forces from ferromagnetic metallic objects, like a transmission shaft, screw driver shaft, torque wrenches, and power-tool drilling shaft, for example.

The first magnetic field generating unit may in particular be a coil applied with a signal in form of alternating current for generating a magnetic field. The force measurement sensor may comprise a flux concentrator, wherein the first magnetic field generating unit may be wound around the flux concentrator, such that the flux concentrator directs the magnetic field lines of the magnetic field generated by the first magnetic field generating unit along the first facing orientation towards the surface of the object to be sensed.

The first magnetic field detector unit may in particular be a coil adapted for generating a current when being applied to the magnetic field lines of the magnetic field generated by the first magnetic field generating unit. The magnetic field lines induce a current to the first magnetic field detector unit.

The direction and strength of the magnetic field lines may vary dependent on an applied force to the object to be sensed. Thus, the current induced to the first magnetic field detector unit corresponds to the first signal which may vary dependent on the mechanical forces applied to the object to be sensed, wherein the current is a scale for the mechanical forces applied to the object to be sensed.

As the first magnetic field detector unit comprises a lateral offset with respect to the poles of the first flux concentrator, the sensitivity of the first magnetic field detector unit may be increased as an axial force may in particular influence or influence with an increased effect magnetic field lines being distant to a central axis of the flux concentrator. Thus, axial forces applied to a longitudinal object may be detected with higher accuracy.

The first flux concentrator may be of a C-shape or any other circular arc shape, wherein the first pole and the second pole are arranged at the two ends of the first flux concentrator. The first pole and the second pole may be adapted and formed to correspond to a surface of the object to be sensed. Thus, a surface of the first pole and of the second pole may be inclined with respect to the first flux concentrator or may be a curved, arched, or bent surface.

As the first flux concentrator is circular arc shaped, both the first pole and the second pole are directed towards the surface of the object to be sensed and thus direct the magnetic flux lines towards and through the object to be sensed.

According to an embodiment of the invention, the first lateral offset is perpendicular to the facing orientation of the first flux concentrator pointing towards a surface of the object.

Thus, when applying a magnetic field whose magnetic field lines pass in longitudinal direction of the first flux concentrator and of the objected to be sensed, the magnetic field lines detected by the first magnetic field detector unit having the lateral offset with regard to the first flux concentrator and in particular the central longitudinal direction of the first flux concentrator, the first magnetic field detector unit is arranged such that the magnetic field lines detected by the first magnetic field detector unit are more curved, i.e. do not pass on a linear way from one pole of the first flux concentrator to the other pole. The more curved the magnetic field lines are, the higher may be the effect of a force in axial direction of the object to be sensed on the magnetic field lines. The magnetic field lines may be distracted or redirected by an applied axial force, such that the changing of the magnetic field strength can be used as a criterion for the applied force.

According to an embodiment of the invention, the first flux concentrator comprises a first pole and a second pole being arranged with respect to each other in a longitudinal direction of the first flux concentrator. The longitudinal axis of the first magnetic field detector unit is parallel to a central axis of the first flux concentrator, which central axis is defined by a symmetry axis between the first pole and the second pole of the first flux concentrator.

The longitudinal axis of the first magnetic field detector unit may in particular be a symmetry axis.

The central axis of the first flux concentrator may in particular pass through surfaces of the first and second pole of the first flux concentrator, i.e. be arranged at a surface of the first flux concentrator which surface points towards the surface of the object to be sensed.

In one embodiment, the first magnetic field detector unit is arranged more distant to the surface of the object to be sensed than the surface of the first and second poles of the first flux concentrator.

According to a further embodiment, the first magnetic field generating unit is formed as a coil and wound around the first flux concentrator.

Thus, the first magnetic field generating unit is adapted to generate a magnetic field whose magnetic field lines are directed between the first and second poles towards and through the object to be sensed.

According to a further embodiment, the force measurement sensor as described above and hereinafter comprises a first electromagnetic interference coil being adapted for measuring electromagnetic fields. The first electromagnetic interference coil is arranged opposite to the first magnetic field detector unit with respect to the first flux concentrator, such that the first electromagnetic interference coil is adapted to detect electromagnetic fields in the surroundings of the first sensing unit. The first electromagnetic interference coil is connected to the evaluation unit and is adapted to provide a signal based on which the evaluation unit compensates the effect of interference fields to the first signal.

The first electromagnetic interference coil detects magnetic fields in the surroundings of the force measurement sensor, which magnetic fields are not generated by the first magnetic field generating unit. As these magnetic fields may also lead to a signal in the first magnetic field detector unit, the first electromagnetic interference coil may enable the evaluation unit to subtract the signal caused by interfering magnetic fields. Thus, only the magnetic field generated by the first magnetic field generating unit leads to a signal detected by the first magnetic field detector unit and corresponding to the applied axial force to the object to be sensed.

According to a further embodiment, the force measurement sensor as described above and hereinafter comprises a first feedback element being connected to the evaluation unit and being adapted to provide a comparative signal, based on which the evaluation unit compensates a varying distance between the force measurement sensor and the object.

The first feedback element may in particular provide the magnetic field strength of the magnetic field conducted through the first flux concentrator. This signal is substantially independent of the distance to an object to be sensed.

The magnetic field and the strength of the magnetic field lines conducted from the two poles through the material of the object to be sensed may vary with a varied distance of the force measurement sensor and in particular of the first flux concentrator from the surface of the object to be sensed, which may influence the measured value of the first signal.

In order to consider the distance between the first flux concentrator and the surface of the object to be sensed and not measuring incorrect values of the applied mechanical or axial force, the feedback element provides a reference value which is to be assessed in relation to the signal detected by the first magnetic field detector unit.

According to a further embodiment of the invention, the feedback element is a coil wound around the flux concentrator.

According to a further embodiment of the invention, the force measurement sensor as described above and hereinafter further comprises a second sensing unit. The second sensing unit comprises a second flux concentrator having a second facing orientation pointing towards a surface of the object, a second magnetic field generating unit being adapted for generating a magnetic field, a second magnetic field detector unit being adapted for detecting a second magnetic field which field being generated by the second magnetic field generating unit and being influenced by the applied force to be measured, wherein the second magnetic field detector unit is further adapted for outputting a second signal being representative for the detected magnetic field. A longitudinal axis of the second magnetic field detector unit is arranged such that a second lateral offset between the longitudinal axis of the second magnetic field detector unit and a central axis of the second flux concentrator is provided. The second lateral offset is perpendicular to a longitudinal direction of the second flux concentrator. The evaluating unit is adapted for evaluating a signal strength of the first signal and the second signal as to determine the applied force based on both the first signal and the second signal.

The second sensing unit is of a similar structure as the first sensing unit. Thus, the description of the first sensing unit applies in an analogous manner to the second sensing unit.

According to a further embodiment of the invention, the second sensing unit is arranged such that the first facing orientation and the second facing orientation intersect under an angle unequal to 0°.

The second magnetic field generating unit and the second magnetic field detector unit may be arranged similar to the first magnetic field generating unit and the first magnetic field detector unit, respectively, with respect to each other and with respect to the object to be sensed.

Thus, the explanations and elucidations with regard to the first magnetic field generating unit and first magnetic field detector unit (which may be referred to as a first sensing unit) apply in an analog manner to the second magnetic field generating unit and to the second magnetic field detector unit (which may be referred to as a second sensing unit).

The first sensing unit and the second sensing unit may be used for providing measurement redundancy and avoiding or minimizing errors in measurement.

In case the object to be sensed is a longitudinal object, the first sensing unit and the second sensing unit may be arranged in longitudinal direction of the object to be sensed opposite to each other, i.e. an angle between the first facing orientation and the second facing orientation is 180°.

In an alternative embodiment, the angle between the first facing orientation and the second facing orientation may be 90° or any angle between 0° and 180°.

Arranging the first sensing unit and the second sensing unit in the longitudinal direction of the object to be sensed opposite to each other means that the first sensing unit and the second sensing unit do not have a lateral offset in direction of the longitudinal direction of the object to be sensed.

However, in an alternative embodiment, the first sensing unit and the second sensing unit may be arranged with respect to the object to be sensed such that they have a lateral offset with respect to each other.

According to a further embodiment of the invention, the first sensing unit is arranged opposite to the second sensing unit such that the first facing orientation and the second facing orientation are opposed to each other and the angle between the first facing orientation and the second facing orientation is 180°.

The distance between the first sensing unit and the second sensing unit may correspond to a width or a diameter of the object to be sensed or may be greater than the width or the diameter of the object to be sensed. In the latter case, at least one of the first sensing unit and the second sensing unit is arranged distant to the surface of the object to be sensed and there is a gap between the surface of the object to be sensed and the at least one of the first sensing unit and the second sensing unit arranged distant to the surface of the object to be sensed.

In an alternative embodiment, the first sensing unit and the second sensing unit may be arranged equidistant to the surface of the object to be sensed, wherein the first sensing unit and the second sensing unit each are spaced apart from the object to be sensed and in particular from the surface of the object to be sensed in different directions, i.e. along the first facing orientation and second facing orientation, respectively.

According to a further embodiment of the invention, the distance between the first sensing unit and the second sensing unit is adapted so as to receive an elongated object.

The object to be sensed may be a prismatic, cylindrical, or conical elongated object, in particular a shaft in a rotating or static state which is adapted to be subjected to a mechanical force.

The first pole and the second pole of the flux concentrator of each the first sensing unit and the second sensing unit may be arranged such that the distance of the first pole and the second pole to the surface of the object to be sensed is the same or different.

According to a further embodiment of the invention, the evaluation unit is adapted to add the second signal to the first signal and to determine the applied force based on the sum of the first signal and the second signal.

The force may in particular be applied in one specific axis in relation to the object, for example perpendicular to a longitudinal direction of the object and in more particular equivalent along a circumference of the object to be sensed. Thus, the first and second sensing units provide a measurement signal from different areas or regions of the surface of the object to be sensed and may allow determining the axial load independent of irregularities in the material of the object to be sensed, for example.

The first and second sensing unit may be arranged opposite to each other, i.e. directed towards each other, such that the object to be sensed may be arranged in between the first and second sensing unit.

According to a further embodiment of the invention, the first lateral offset projects from the first flux concentrator in a clockwise direction with respect to the central axis of the first flux concentrator and the second lateral offset projects from the second flux concentrator in a clockwise direction with respect to the central axis of the second flux concentrator.

With respect to a central axis of the object to be sensed, the first magnetic field detector unit and the second magnetic field detector unit may be arranged with respect to the first and second flux concentrator such that the first magnetic field detector unit and the second magnetic field detector unit are arranged opposite to each other with respect to the central axis, i.e. the parallel offset of the first magnetic field detector unit and the second magnetic field detector unit is of the same amount. The central axis of the object to be sensed intersects with an interconnection line between the first magnetic field detector unit and the second magnetic field detector unit.

According to a further embodiment of the invention, one of the first lateral offset and the second lateral offset projects from the first or second flux concentrator, respectively, in a clockwise direction with respect to the central axis of the first or second flux concentrator, respectively, wherein the other one of the first lateral offset and the second lateral offset projects from the first or second flux concentrator, respectively, in a counterclockwise direction with respect to the central axis of the first or second flux concentrator, respectively.

In this embodiment, an interconnection line between the first magnetic field detector unit and the second magnetic field detector unit does not intersect with the central axis of the object to be sensed but is skew with respect to the central axis of the object to be sensed.

According to a further embodiment of the invention, at least one of the first magnetic field detector unit and of the second magnetic field detecting unit comprises a coil which is located between the first pole and the second pole.

The coil is arranged for detecting the magnetic field lines of the magnetic field generated by the first magnetic field generating unit and the second magnetic field generating unit. The magnetic conductivity of the object to be sensed may vary dependent on an applied force to the object to be sensed such that the magnetic field strength detected by the first magnetic field detector unit and the second magnetic field detector unit and in particular by the coil of the detector units varies.

As the coil is arranged in between the first pole and the second pole, the coil may optimally detect the changed magnetic conductivity which leads to a changed magnetic field strength between the poles, as the magnetic field may be distracted by the object to be sensed in case the object to be sensed is subjected to a mechanical force.

According to a further aspect of the invention, a force measurement arrangement for measuring an applied force onto an object is provided. The force measurement arrangement comprises a force measurement sensor as described above and hereinafter and an object to be measured, which object has a longitudinal axis. The longitudinal axis of the object is parallel to the longitudinal direction of the first flux concentrator.

The force measurement arrangement may comprise a fixture apparatus for fixing the object such that the longitudinal axis of the object is aligned with the longitudinal direction of the flux concentrator.

According to a further embodiment of the invention, the object is a rotating shaft. The rotating shaft may in particular rotate around the longitudinal axis, i.e. the longitudinal axis is the rotational axis.

In one embodiment, the force measurement sensor as described above and hereinafter may be a non-contact sensor which does not require a direct connection to the test object and may enable direct, proportional and linear measurement of axial forces. The force measurement sensor may be insensitive to cross talk caused by other mechanical forces, like torque and bending, wherein the sensor performance may be insensitive to age and to any interfering magnetic fields. The force measurement sensor may work with any ferromagnetic material and in particular with commercially available industrial steels. The object to be sensed can freely rotate and move back and forth beneath the sensor module without interfering with the axial load measurement. The force measurement sensor may provide a large signal range and a good signal-to-noise ratio. While strain gauge sensors may provide a signal of a few mV only (when measuring axial load directly), the force measurement sensor as described above and hereinafter may provide 100 mV to 500 mV of signal directly, without any amplification. The sensor can detect changes caused by operational temperatures, assembly tolerances, changes in the placement of the sensor in relation to the object to be sensed, and aging of components (generator signal, for example). The force measurement sensor may be insensitive to any static magnetic field that may be accidentally stored in the object to be sensed or caused by strong magnets that will be attached to the test object (limits apply).

The force measurement sensor may be applicable for measuring load forces on building structures, like skyscrapers, bridges, suspension systems, mining and drilling, i.e. for detecting mechanical forces in drilling shaft, in the transportation sector for detecting structural load in planes, trains, commercial trucks, and cars, in cranes for measuring load forces and monitoring safety limits, in power tools for measuring drilling and chiseling forces.

The sensor system as described above and hereinafter may be sensitive to external magnetic stray fields, when hitting the same frequency as the operational frequency of this sensor. There are several solutions applicable to eliminate the unwanted effects caused by interfering signals: magnetic shielding, adding one more level of differential mode magnetic field sensing devices (which will compensate for the effects of EMI), or frequency hopping of the sensor system.

When applying magnetic shielding (which may always be an effective method of protecting the sensor from interfering magnetic stray fields) it may be important that the magnetic shielding applied is not miss-guiding or bending the magnetic flux lines needed for the sensor to function.

Differential mode compensation coils may be the preferred solution to eliminate or compensate for the unwanted effects caused by magnetic EMI. In this case an additional magnetic sensing device, i.e. an EMI detection coil, will be placed in reverse position to the main sensing device, i.e. to the first magnetic field detector unit and connected in series to each other. While the first magnetic field detector unit is responsible to measure the signal changes caused by the axial load changes and will also measure the EMI signals, the EMI detection coil measures mainly the EMI signals in the same phase and amplitude. As the two sensing devices are connected to each other in series, the EMI signals cancel each other while the axial load signal will be dampened a little only.

Frequency Hopping means that the force measurement sensor as described above and hereinafter is changing its operational frequency ever so often, within the frequency range this sensor will function. As an example, a micro controller unit (MCU) generates in succession the operational frequencies (needed to drive the first magnetic field generating unit) from the F1, to F2, and then to F3. After the frequency F3 the MCU begins with F1 again.

When pausing at a certain operational frequency, the MCU takes the measurements from the first magnetic field detector unit and is later comparing this measurement with measurements taken at the other two operational frequencies (F2, and F3). By comparing the three measurements with each other (under normal circumstances they should be all identical) it is possible to identify the measurement that is incorrect as a potential interfering magnetic signal, at one specific frequency, interfered with this one measurement: Two-out-of-Three measurements have to match in order to be sure about a faulty measurement.

The force measurement sensor can be designed and produced in different dimensions and with this may define the sensor signal performances (like signal amplitude, measurement hysteresis, signal offset, sensitivity to cross-talk forces, signal-to-noise ratio, for example).

The sensor system performance may increase when the inductivity of the first magnetic field detector unit is increasing (in the area of 20 mH to 200 mH) and at the same time the physical dimensions of the inductivity becoming smaller. It may not help to use a physical large inductor, where large parts of the inductors body are reaching outside of the to-be-measured magnetic flux lines.

When using hardened shaft material (in comparison to unhardened test object material) the potentially relative large measurement hysteresis may become smaller, and eventually will disappear to a non detectable level. In many cases, hardening the test object material (at least at the sensing location) may also reduce the signal gain. However, the gained signal quality (low hysteresis, high linearity) may make this worthwhile.

Exemplary embodiments of the invention will be described with reference to the following drawings.

DETAILED DESCRIPTION OF EMBODIMENTS

Figure 1:
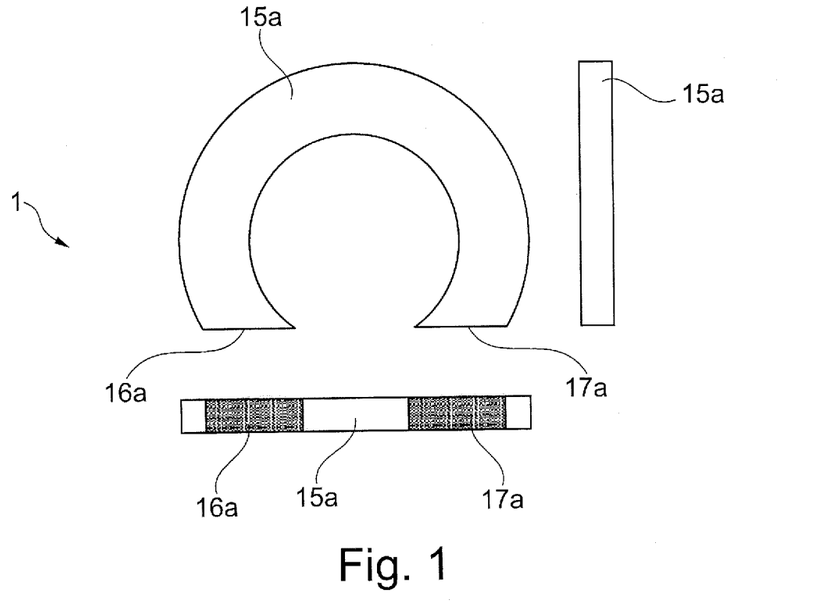
FIG. 1 illustrates a flux concentrator of a force measurement sensor according to an exemplary embodiment of the invention.

FIG. 1 illustrates a three-side view of a first flux concentrator 15a of a force measurement sensor 1. The first flux concentrator 15a has a first pole 16a and a second pole 17a. The surfaces of both poles 16a, 17a are pointing in the same direction, i.e. in the first facing direction.

As will be described in more detail below, the surfaces may be arranged within the same plane or may be parallel to each other. In an alternative embodiment, the surfaces of the poles may be inclined to each other.

The flux concentrator is shaped in form of a C-shape or U-shape, and in particular in form of an arc of a circle. The surface of the first pole and of the second pole may be adapted to the surface of the object to be sensed, i.e. the surface of the poles is also circular shaped and in particular concave.

The first flux concentrator with the generator coil wound around it has the task to produce and to maintain a controlled and active magnetic field path beneath the surface of the object to be sensed. The simplest and efficient way of such a flux concentrator may be to use a washer (tooled from ferromagnetic material, for example) where one side has been tooled off.

A number of coils (first magnetic field generating unit and first feedback element) are then wound around the remaining body of the flux concentrator that are needed to generate an active (alternating) magnetic field and to regain information of the sensors efficiency.

Figure 2:
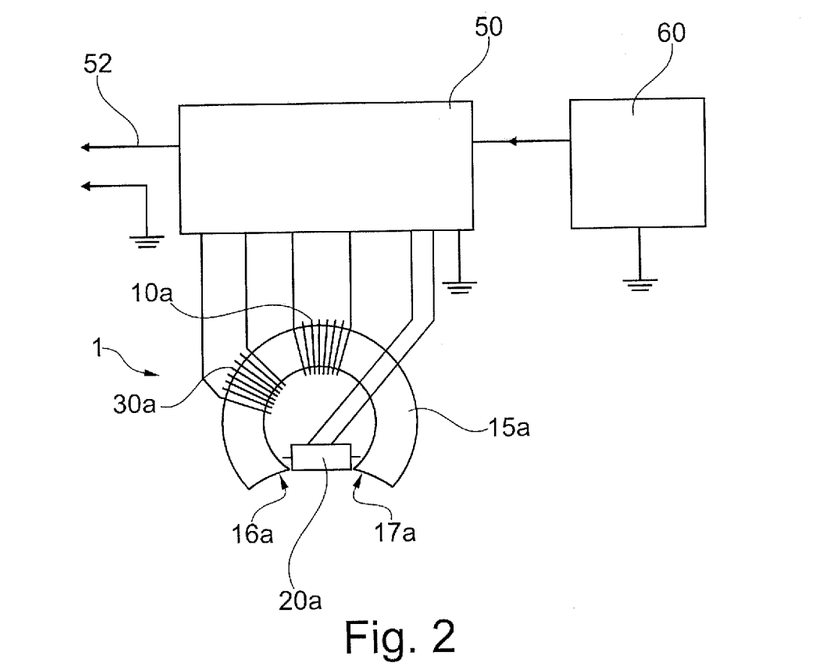
FIG. 2 illustrates a force measurement sensor according to a further exemplary embodiment of the invention.

FIG. 2 illustrates a force measurement sensor 1 having a first sensing unit with a first flux concentrator 15a with a first and a second pole 16a, 17a, a first magnetic field generating unit 10a, a first magnetic field detector unit 20a, and a first feedback element 30a.

The first magnetic field generating unit and the first feedback element are formed as coils and wound around the first flux concentrator 15a. The first magnetic field detector unit 20a is formed as a coil and arranged between the poles 16a, 17a of the first flux concentrator such that a longitudinal axis of the first magnetic field detector unit extends in a direction from one of the poles to the other one of the poles.

The first magnetic field generating unit 10a is driven with an alternating current and generates a magnetic field whose magnetic field lines are concentrated and directed towards the object to be sensed. The magnetic field lines spread through the object to be sensed from one of the poles to the other one of the poles, wherein the magnetic flux depends on a mechanical force applied to the object to be sensed 2.

The first feedback element 30a is adapted to measure the magnetic field strength of the magnetic field flowing through the first flux concentrator.

Between the first pole and the second pole, the first magnetic field detector unit 20a is arranged such that magnetic field lines between the first pole and the second pole lead to an induced current in the first magnetic field detector unit in form of a coil. As the magnetic field strength between the first pole and the second pole varies dependent on a mechanical force applied to the object to be sensed, the current induced into the first magnetic field detector unit varies and is a parameter for the mechanical force and in particular axial load force applied to the object to be sensed.

The first magnetic field detector unit is arranged such that a longitudinal axis of the first magnetic field detector unit extends parallel to a longitudinal axis of the object to be sensed.

FIG. 2 illustrates a schematic overview of a force measurement sensor 1, wherein the first magnetic field generating unit 10a and the feedback element 30a as well as the first magnetic field detector unit 20a are connected to the evaluating unit 50 which on the one hand generates the signal transmitted to the first magnetic field generating unit for generating the magnetic field and senses the signal transmitted by the first feedback element and the first magnetic field detector unit for determining the mechanical force and in particular the axial force applied to the object to be sensed.

The evaluating unit 50 receives electrical power from the power supply 60 and provides the output signal which indicates the force applied to the object to be sensed at the output line 52.

The sensor consists of two main modules: the actual sensing element (built by using passive electronic components), and the sensor electronics. Both modules can be placed together in the same housing, but can also be placed separately from each other, only connected to each other by a number of wires, for example wires of a length up to a few meters, in particular between 1 m and 5 m, an in particular 2 m.

The contactless force measurement sensor consists of several modules: sensor hardware (flux concentrator, generator coil, feedback coil, detector coil); an electronic circuit of the evaluating unit; a six lead connection cable or line between the sensor hardware and the electronics of the evaluating unit; a power supply and a two lead connection cable or line between the electronics and the power supply.

A complete and single sensing element consists of all the components shown above. The feedback coil is optional and may be required only when any potential spacing changes between the object to be sensed and the contactless force measurement sensor has to be compensated automatically. The function of the feedback coil may be used only when driving the field generator coil with an AC driver signal. When using a DC current driver signal, the automatic space compensation feature may not be realized by the feedback coil.

The optional feedback coil is used to detect and measure the spacing or the gap between the contactless force measurement sensor and in particular the flux concentrator and the surface of the object to be sensed. The signal measured with this coil will be used to compensate for the unwanted signal amplitude modulation caused when the spacing between the object to be sensed and the contactless force measurement sensor keeps changing. In application where the spacing is not changing, the feedback coil may not be required. The feedback coil provides precise information about the sensor efficiency or when the spacing between the sensor hardware and the surface of the object to be sensed is changing.

In the spacing between the two magnetic pole ends of the flux concentrator, the magnetic field sensor, i.e. the first magnetic field detector unit, is placed. The magnetic field sensor can be anything that is capable to measure accurately the magnetic field strength of a magnetic field in the area of +/−50 Gauss or less. This includes, but is not limited to inductors, hall-effect, magneto resistive material, or giant magneto resistive material, for example.

Several sensor performances may be defined by the physical dimension and the used material of the flux concentrator. For performance reasons (high efficiencies and availability of the material) transformer sheet can be used that are cut or tooled to the right size and shape. While a round shape may be more preferred from the physics point of view, other shapes may be more practical in order to minimize the space required by the sensor module.

The thickness of the flux concentrator has to be in relation to the used magnetic field sensing device, but in general the flux concentrator may be very thin. When the flux concentrator thickness is getting to large then the ability of measuring the directional sensitive axial load signal may be diminishing, i.e. that the sensor may in addition to axial loads detect other mechanical forces as well like bending and torque forces.

Figure 3:
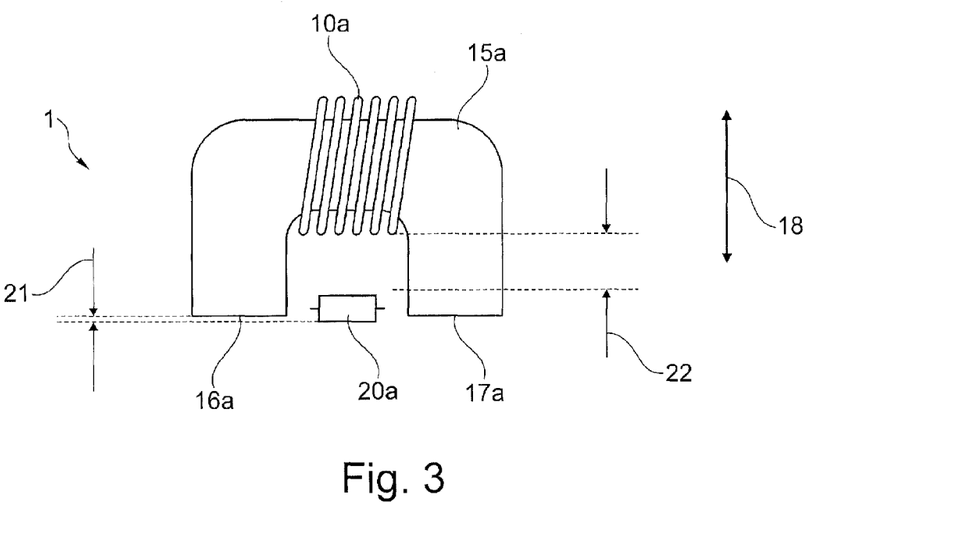
FIG. 3 illustrates a force measurement sensor according to a further exemplary embodiment of the invention.

FIG. 3 illustrates a force measurement sensor 1 comprising a first flux concentrator 15a with a first magnetic field generating unit 10a and a first magnetic field detector unit 20a.

The poles 16a, 17a of the first flux concentrator 15a are configured to be arranged opposite to a surface of an object to be sensed, wherein the distance 21 between the poles 16a, 17a and the surface of the object to be sensed may in one embodiment be very small, for example less than 1 mm or 2 mm. In the same manner, the first magnetic field detector unit 20a may also be arranged close to the surface of the object to be sensed. Additionally, the distance 22 represents the height offset in direction of the height direction 18 between the first magnetic field detector unit 20a and the first magnetic field generating unit 10a or the first flux concentrator 15a in a direction along the first facing orientation or perpendicular to the surface of the object to be sensed.

The lateral offset of the longitudinal axis of the first magnetic field detector unit and the central axis of the first flux concentrator is an offset in a direction out of the or into the drawing plane of FIG. 3.

In one embodiment, the surface of the poles is adapted such that the distance between the surface of the poles and a surface of the object to be sensed is even over the entire pole surface area. In case the longitudinal direction of the flux concentrator is parallel to the longitudinal axis of the object to be sensed, the surface of the poles is even.

The distance 22 between the first magnetic field generating unit and the first magnetic field detector unit may in particular be adapted such that a direct coupling of the generator coil field and the first magnetic field detector unit is less than the magnetic field strength measured in the object to be sensed.

Figure 4A:
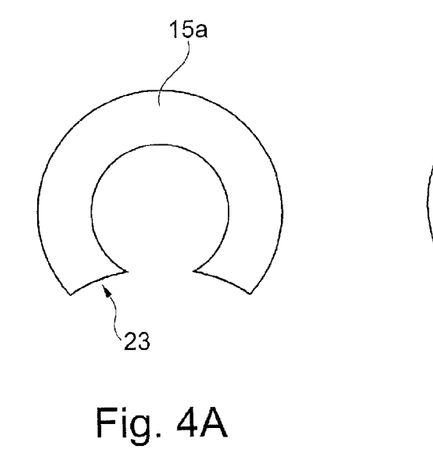
FIG. 4A schematically illustrates a flux concentrator of a force measurement sensor according to a further exemplary embodiment of the invention.
Figure 4B:
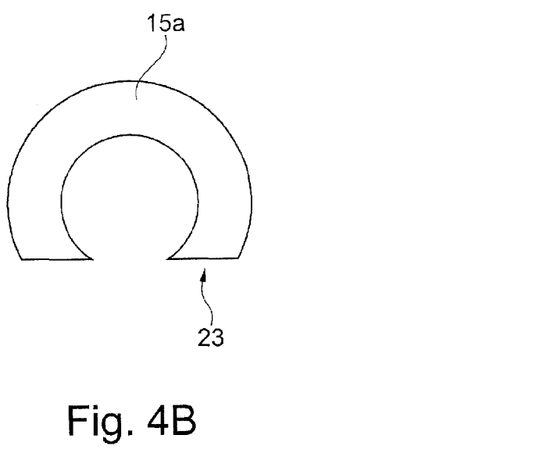
FIG. 4B schematically illustrates a flux concentrator of a force measurement sensor according to a further exemplary embodiment of the invention.

FIGS. 4A and 4B illustrate possible forms of the flux concentrator. As there are two specific directions the force measurement sensor can be placed in relation to the object to be sensed, there are two different ways the flux concentrator poles may be shaped.

FIG. 4A illustrates a flux concentrator which comprises rounded pole surfaces and is adapted for being arranged cross to a longitudinal axis of the object to be sensed.

FIG. 4B illustrates a flux concentrator having even pole surfaces being arranged in a plane or in other words at the same height in height direction of the flux concentrator, such that the longitudinal direction of the flux concentrator from one pole to the other is arranged parallel to a longitudinal axis of the object to be sensed.

The flux concentrator shown in FIG. 4B may be the preferred embodiment for a force measurement sensor for measuring axial load forces.

Figure 5A:
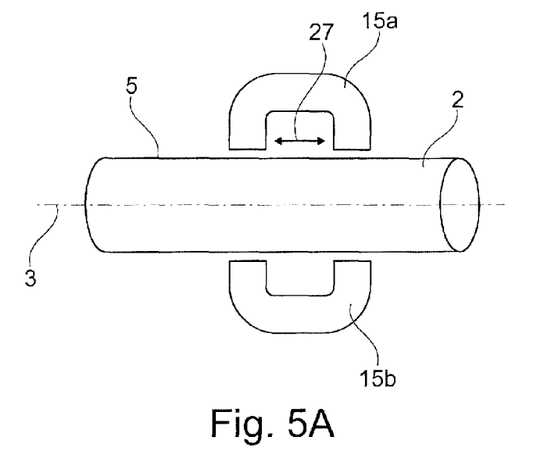
FIG. 5A schematically illustrates a front view of a force measurement sensor according to a further exemplary embodiment of the invention.

FIG. 5A illustrates a schematic front view of a force measurement sensor 1 having a first and a second sensing unit which are placed opposite to each other such that the object to be sensed 2 is arranged in between the first and the second sensing unit.

The longitudinal direction 27 of the first and second flux concentrators 15a, 15b is parallel to the longitudinal axis 3 of the object to be sensed 2. The flux concentrators are arranged perpendicular with respect to a surface 5 of the object to be sensed.

Figure 5B:
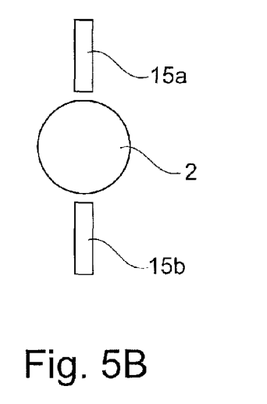
FIG. 5B schematically illustrates a side view of the force measurement sensor of FIG. 5A.

FIG. 5B illustrates a side view of the force measurement sensor shown in FIG. 5A. It can be seen that the first flux concentrator 15a and the second flux concentrator 15b have no lateral offset with respect to each other, i.e. both are perpendicular to the surface of the object to be sensed and the according height directions of the first and second flux concentrators are parallel to each other and more precisely coincide when elongated.

Through the flux concentrator of each individual sensing device (with two magnetic poles), a defined alternating magnetic field is conducted into the object to be sensed. In the spacing between the magnetic poles a magnetic field detector unit is placed that is measuring the flux density in air between the two poles. When the two magnetic poles are placed in a fixed distance, in relation to the surface of the object 2 (zero to 2 mm distance, for example), then the magnetic flux lines generated by the magnetic field generator will be partially absorbed by the ferromagnetic object 2. Depending on the axial forces applied to the object, the ability of absorbing these alternating magnetic flux lines will change proportionally.

Figure 8A:
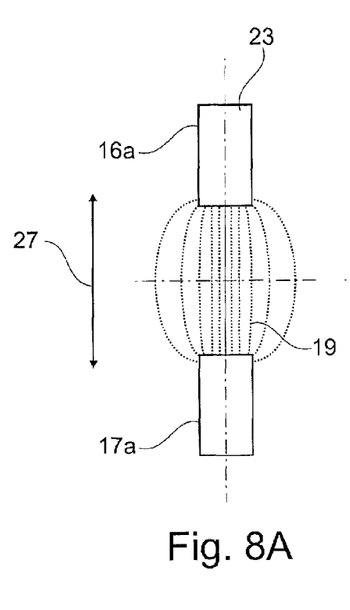
FIG. 8A schematically illustrates the gradient of the magnetic field lines applied to an object to be sensed.
Figure 8B:
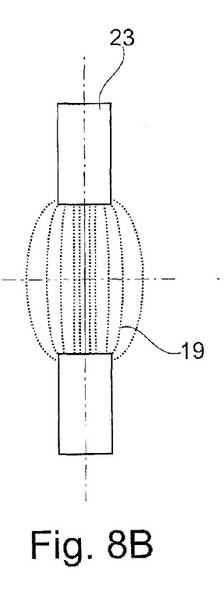
FIG. 8B schematically illustrates the gradient of the magnetic field lines applied to an object to be sensed.
Figure 8C:
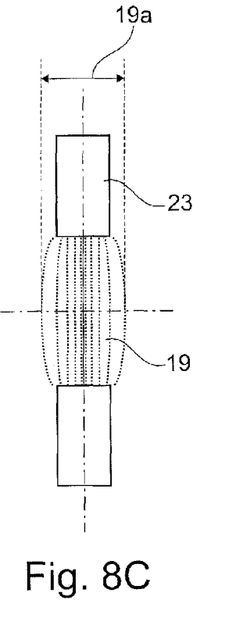
FIG. 8C schematically illustrates the gradient of the magnetic field lines applied to an object to be sensed.

When the object 2 will be stretched (trying to elongate the object without entering the stage of plastic deformation of the object) then the ability to absorb the magnetic flux lines does increase (meaning that there will be fewer magnetic fields to measure by the first magnetic field detector unit) This situation is shown in FIG. 8C. In reverse, when putting pressure on both ends of the object (applying axial load forces, see FIG. 8A) then the ability of the object of absorbing the magnetic flux lines (generated by the first magnetic field generating unit) will decrease. In this case the magnetic field density at the surface of the object, where the first magnetic field detector unit is placed, will increase.

The force measurement sensor consists of two identical flux concentrators (fully assembled) placed opposite to each other at the symmetrically shaped object 2. The coils (inductors) that are wound around each flux concentrator are connected with each other and then connected to the sensor electronics.

"Two" sensing modules may be useful for differentiating between bending forces and axial load forces. When using only one sensor module it may not be possible to tell what the cause may be for the measurement signals: It could be a bending force that is applied to the test object, or it could be an axial load force. However, the signal strength caused by bending forces may be in the area of 60 to 70 times larger than the signal strength caused by axial load forces.

Figures 6A, 6B:
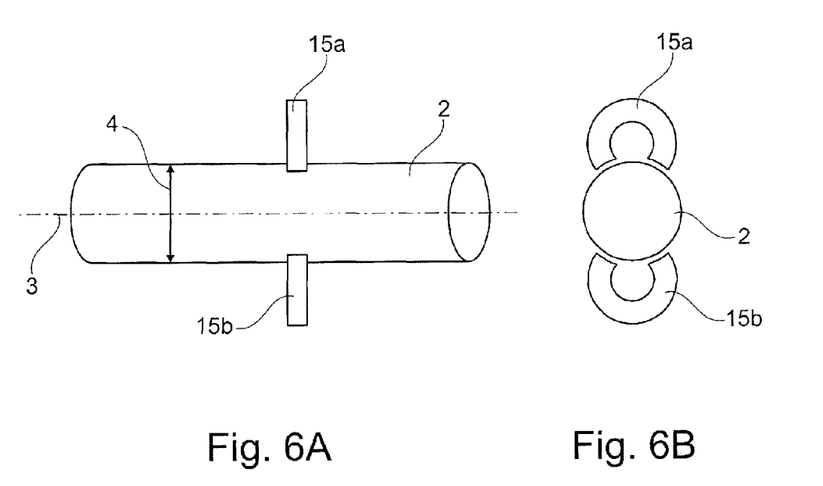
FIG. 6A schematically illustrates a front view of a force measurement sensor according to a further exemplary embodiment of the invention.
FIG. 6B schematically illustrates a side view of the force measurement sensor of FIG. 6A.

FIGS. 6A and 6B illustrate a force measurement sensor 1 wherein the longitudinal direction between the poles of the first and second flux concentrators is perpendicular to the longitudinal axis of the object to be sensed. The surfaces of the flux concentrators may be adapted to a surface of the object to be sensed, i.e. having a rounded cross section which is adapted to the rounded surface of the object to be sensed and which may in particular be adapted to the diameter 4 of the object to be sensed.

Figure 7A:
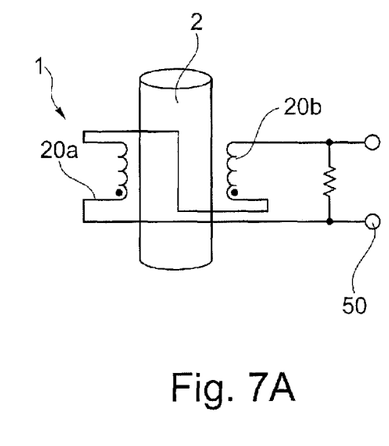
FIG. 7A schematically illustrates a force measurement sensor according to a further exemplary embodiment of the invention.
Figure 7B:
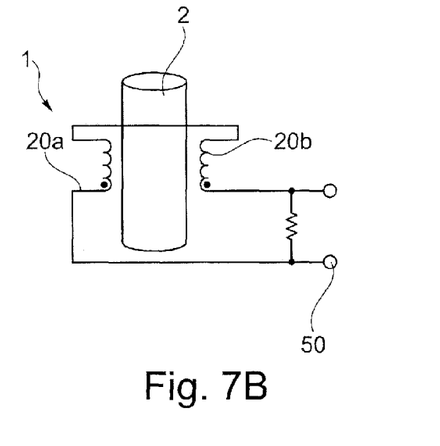
FIG. 7B schematically illustrates a force measurement sensor.

FIGS. 7A and 7B illustrate a schematic electrical interconnection of the evaluation unit 50 and the first magnetic field detector unit 20a and the second magnetic field detector unit 20b.

In FIG. 7A, the first magnetic field detector unit and the second magnetic field detector unit are interconnected such as to sum up the signals of the first and second magnetic field detector units. This interconnection of the first magnetic field detector unit and the second magnetic field detector unit may be the preferred interconnection for measuring axial load forces.

The force measurement sensor shown in FIG. 7B may additional be sensitive to bending forces applied to the object to be sensed, as the first and second signal of the first magnetic field detector unit and the second magnetic field detector unit are being subtracted from each other, whereas axial loads are applied to the object to be sensed in a circumference direction in the same manner such that an addition of the first and second signal as shown in FIG. 7A may be preferred for measuring axial loads.

FIGS. 8A, 8B, and 8C schematically illustrate the spread 19a or course of the magnetic field lines 19 between the first pole 16a and the second pole 17a and through an object to be sensed when applying an axial force to the object to be sensed, i.e. a force in a direction 27 from one of the first pole and the second pole to the other one of the first and second poles.

FIG. 8A illustrates the spread of the magnetic field lines when applying a compressive force along the direction 27 to the object to be sensed. The spread 19a of the magnetic field 19 is broadened when being compared to an unloaded object to be sensed (see FIG. 8B) or to an object to be sensed subjected to tensile force (see FIG. 8C), wherein the spread 19a is the narrowest when applying a tensile force, as shown in FIG. 8C.

The largest influential factor that decides about the performance of the force measurement sensor may be the placement and orientation of the first magnetic field detector unit. Even the smallest movement in any direction or smallest rotational change of the sensitivity axis of the first magnetic field detector unit may have great effects on the achievable signal gain and the sensitivity to cross talk forces (like bending and torque forces).

As illustrated in FIGS. 8A, 8B, and 8C, the magnetic flux lines that can be detected at the surface of the object to be sensed between the two poles of the flux concentrator remain almost constant in the geometric center between the poles of the flux concentrator. Thus, the placement of the first magnetic field detector unit may be optimal when having a lateral offset as described above and hereinafter with respect to the central axis of the flux concentrator.

The spread 19a of the detectable magnetic flux lines is widening when the object to be sensed is compressed (axial load forces are applied to both ends of the test object towards each other, see FIG. 8A), and the area where the magnetic flux lines are traveling between the two pole faces will narrow when axial pulling (stretching, the both ends of the test object are being pulled away from each other, see FIG. 8C) forces are applied at both ends of the object to be sensed.

Figure 9A:
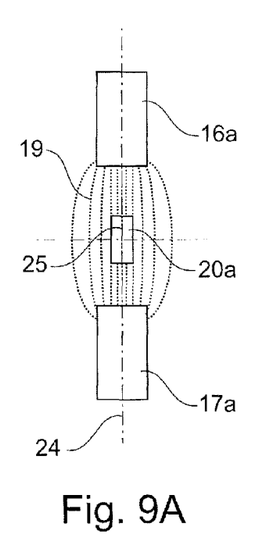
FIG. 9A schematically illustrates the gradient of the magnetic field lines applied to an object to be sensed and a magnetic field detector unit of a force measurement sensor.
Figure 9B:
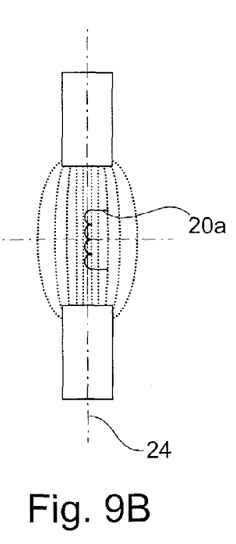
FIG. 9B schematically illustrates the gradient of the magnetic field lines applied to an object to be sensed and a magnetic field detector unit of a force measurement sensor.
Figure 10:
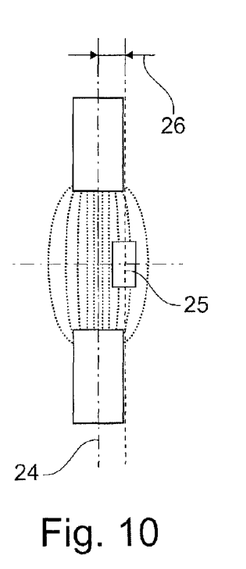
FIG. 10 schematically illustrates the gradient of the magnetic field lines applied to an object to be sensed and a magnetic field detector unit of a force measurement sensor according to a further exemplary embodiment of the invention.

FIGS. 9A, 9B, and 10 illustrate the effect of placing the first magnetic field detector unit with a lateral offset between the longitudinal axis 25 of the first magnetic field detector unit 20a and the central axis 24 of the flux concentrator and according with a lateral offset with respect to the geometric center of the magnetic field 19 between the two poles 16a, 17a of a flux concentrator.

When applying an axial force, the flow direction of the magnetic field may change minimal along the central axis 24 of the flux concentrator. The measuring signal may provide a small signal range and thus may not provide accurate force measurement results when placing the first magnetic field detector unit 20*a* at the central axis 24, as shown in FIGS. 9A and 9B.

In contrary to that, when providing a lateral offset 26 between the central axis 24 of the flux concentrator and the longitudinal axis 25 of the first magnetic field detector unit 20*a* as shown in FIG. 10, the magnetic field lines may be subjected to more spread when applying an axial force to the object to be sensed such that the measuring signal may have a higher signal range and thus may provide a more accurate force measurement.

Figure 11A:
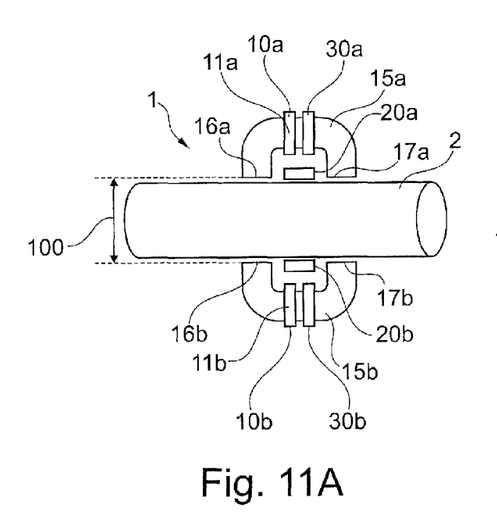
FIG. 11A schematically illustrates a front view of a force measurement sensor according to a further exemplary embodiment of the invention.
Figure 11B:
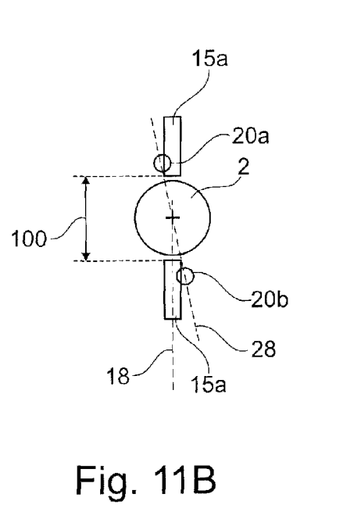
FIG. 11B schematically illustrates a side view of the force measurement sensor of FIG. 11A.

FIGS. 11A and 11B illustrate a front view and a side view of a force measurement sensor 1 having a first and a second sensing unit as already shown in and described with relation to FIGS. 5A and 5B.

The first sensing unit and the second sensing unit are arranged distant to each other with the distance 100 between the surfaces of the poles 16*a*, 17*a* and 16*b*, 17*b* of the first flux concentrator 15*a* and second flux concentrator 15*b*, respectively.

Each of the first and second flux concentrator has a first magnetic field generating unit 10*a*, 10*b* and a feedback element 30*a*, 30*b*.

In one embodiment, the feedback elements 30*a*, 30*b* may be arranged close to one of the poles of the respective flux concentrator or even at the poles of the respective flux concentrator. In other words, the feedback elements may be located as far away from the magnetic field generating units 10*a*, 10*b* but still at or on the respective flux concentrator.

The first magnetic field detector unit 20*a* and the second magnetic field detector unit 20*b* each are arranged with respect to the first flux concentrator 15*a* and the second flux concentrator 15*b* such that a lateral offset is provided between the central axis of the flux concentrators and the longitudinal axis of the first magnetic field detector unit and the second magnetic field detector unit, respectively. The detector units 20*a*, 20*b* both have a lateral offset in counterclockwise direction with regard to the according flux concentrator.

The first and second sensing unit may be arranged such that the according height directions 18 of the flux concentrators are parallel to each other.

Figure 12:
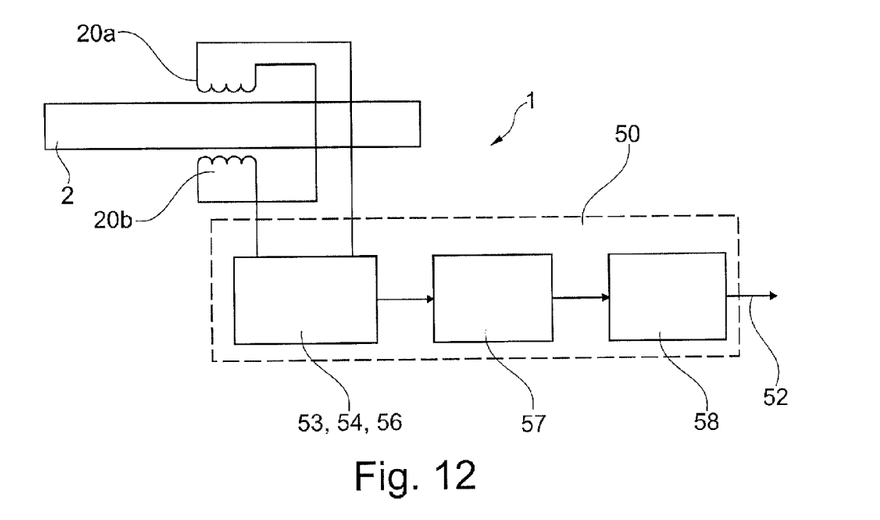
FIG. 12 illustrates a force measurement sensor according to a further exemplary embodiment of the invention.

FIG. 12 illustrates a schematic overview of the electrical interconnection when using the differential measurement mode. The signals of both the first magnetic field detector unit 20*a* and the second magnetic field detector unit 20*b* are detected and lead to the evaluating unit 50, wherein the signals are processed or directed to an AD converter 57 and a micro controller unit 58 in order to generate the output signal 52.

In case the first magnetic field detector unit and the second magnetic field detector unit are of identical specifications with regard to inductivity and physical dimensions, the coils can be connected to each other in series, but one may be connected in reverse order which allows that the signals measured in the first magnetic field detector unit and in the second magnetic field detector unit will be subtracted from each other before the signal will be fed into the signal conditioning and signal processing module of the evaluating unit 50.

It should be noted that the coils of the first magnetic field detector unit 20*a* and the second magnetic field detector unit 20*b* may also be connected such that their respective signals are being summed up.

Figure 13:
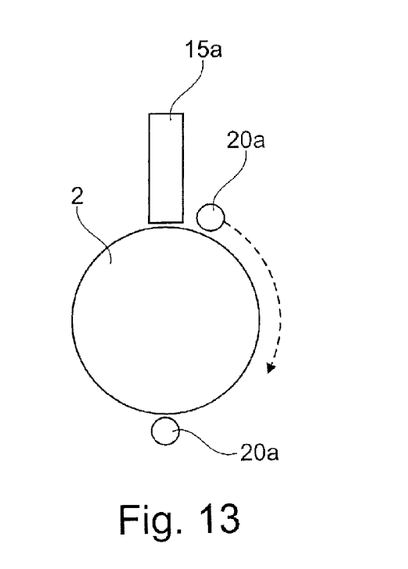
FIG. 13 illustrates a force measurement sensor according to a further exemplary embodiment of the invention.

FIG. 13 illustrates a force measurement sensor having a single sensing unit with a flux concentrator 15*a* and a first magnetic field detector unit 20*a*, wherein the first magnetic field detector unit may be optionally placed at different positions with regard to the flux concentrator along the surface of the object to be sensed 2.

When using only one sensing module then the first magnetic field detector unit 20*a* may be placed almost anywhere around the test object in order to obtain a good signal that is influenced by the mechanical forces applied to the object 2. Of course the dimensions of the used flux concentrator and the magnetic field strengths provided by the first magnetic field generating unit may have to be proportional to the physical size of the object to be sensed.

While this design option may be less attractive to large diameter shafts, it is a great solution when the shaft diameter is in the area of 50 mm and below.

Figure 14:
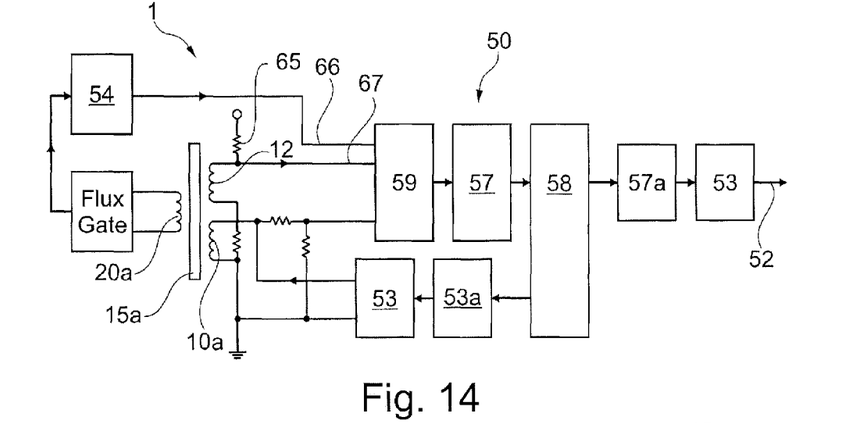
FIG. 14 illustrates a force measurement sensor according to a further exemplary embodiment of the invention.

FIG. 14 illustrates a schematic overview of the force measurement sensor signal electronics and the evaluation unit 50.

The first flux concentrator 15*a* has a first magnetic field generating unit 10*a*, a first magnetic field detector unit 20*a* and a compensation coil 12, wherein the first magnetic field detector unit is connected to a signal filter 54 via a flux gate. The signals from the filter 54, from the compensation coil 12, and from the first magnetic field generating unit 10*a* are provided to a multiplexer 59, which further provides the signals to an AD-converter, a micro controller unit 58, a DA-converter 57*a* and last to an output filter 53.

The driving signal of the first magnetic field generating unit 10*a* is provided to the compensation coil 12 and to the first magnetic field generating unit 10*a* by the micro controller unit 58 via a power driver 53*a* and an input filter 53.

The here described signal conditioning and signal processing electronics may be only one of several possible solutions. A micro controller generates the desired generator driver signal (specific audible frequency) that is then amplified (current driver) and filtered before connected to the first magnetic field generating unit 10*a*. Best may be to use a sinus shaped signal as it may cause the lowest possible unwanted interferences within and outside of the sensor system.

To compensate for the strong signal amplitude changes (depending on the spacing between the flux concentrator pole faces and the object's surface), a compensation coil 12 will measure the "effective" magnetic transmission within the flux concentrator. The compensation coil 12 and the first magnetic field generating unit 10*a* are two coils that are wound around the flux concentrator device. When the spacing is increasing between the pole surfaces and the object surface, then the signal received by the compensation coil 12 is getting smaller.

When the spacing is getting smaller, then the signal measurable at the compensation coil 12 is getting larger. The signal measured at the compensation coil 12 is then allowing compensating for the signal changes resulting at the first magnetic field detector unit.

The resistor 65 is conducting a DC current through the compensation coil 12. As long as the supply voltage at the resistor 65 is known or constant, the attenuated DC signal portion measured at the second multiplexer input 67 will change in relation to the operating temperature that is acting on the copper wires of the compensation coil 12. The higher the operating temperature, the larger the DC voltage that can be measured at the second multiplexer input 67.

The magnetic field sensing circuit used is suitable for use with flux gate electronics. A flux gate detection circuit is very sensitive and provides a relative large signal (in relation to the applied axial load forces). However, the flux gate circuit can be easy saturated when the magnetic fields to be measured are getting large. In addition, a flux gate circuit may add negatively to the signal-to-noise ratio.

An alternative embodiment may be to use a standard inductor as the first magnetic field detector unit and to pass the signal received there, either straight in to the first input 66 of the multiplexer 59 and into the analogue input of the AD-converter 57, or to filter and to amplify the signal first to the desired levels. This solution may generate less noise and may improve the signal-to-noise ratio in the positive direction.

Figure 15A:
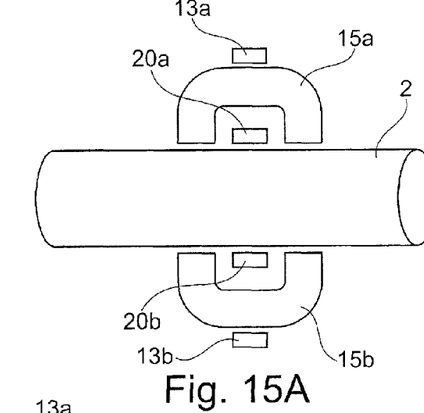
FIG. 15A schematically illustrates a front view of a force measurement sensor according to a further exemplary embodiment of the invention.
Figure 15B:
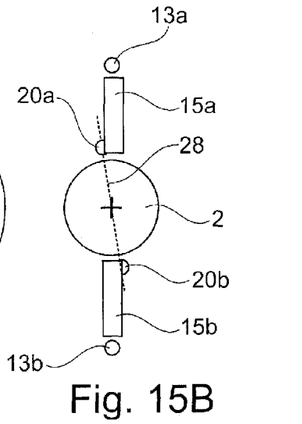
FIG. 15B schematically illustrates a side view of the force measurement sensor of FIG. 15A.

FIGS. 15A and 15B illustrate a front view and a side view of a force measurement sensor having a first and second sensing unit, wherein each of the sensing units comprises an electromagnetic interference detection coil 13*a*, 13*b*, respectively. The first and second electromagnetic interference detection coils are located more distant to the surface of the object to be sensed than the first and second magnetic field detector units 20*a*, 20*b* and particularly above the first and second flux concentrator with regard to the surface of the object to be sensed.

Figure 16:
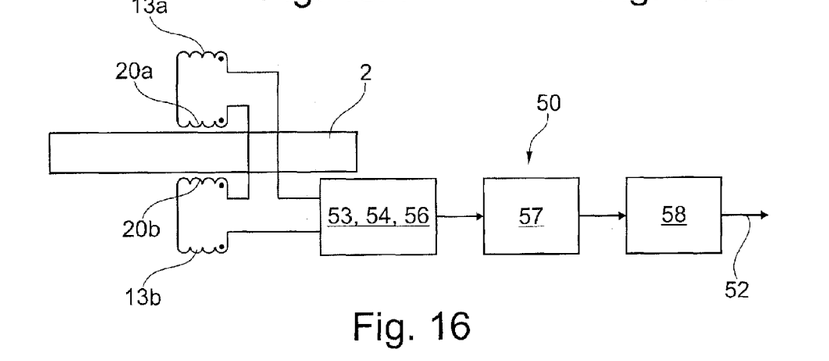
FIG. 16 illustrates a force measurement sensor according to a further exemplary embodiment of the invention.

FIG. 16 illustrates a schematic overview of the sensor electronics of the force measurement sensor shown in FIGS. 15A, 15B.

The evaluation unit 50 considers the signals of the first and second electromagnetic interference detection coils 13*a*, 13*b* and of the first and second magnetic field detector units 20*a*, 20*b*, respectively in order to determine a genuine force measurement signal free of any distortion or interference signals, wherein in particular the signals from the first and second electromagnetic interference detection coils are subtracted from the measurement signals of the first and second magnetic field detector units.

The invention claimed is:

1. A force measurement sensor for measuring an applied force onto an object, comprising:
    a first sensing unit including (a) a first flux concentrator having a first facing orientation pointing towards a surface of the object; (b) a first magnetic field generating unit being adapted for generating a magnetic field; (c) a first magnetic field detector unit being adapted for detecting a first magnetic field which field being generated by the first magnetic field generating unit and being influenced by the applied force to be measured, wherein the first magnetic field detector unit is further adapted for outputting a first signal being representative for the detected magnetic field; and (d) an evaluating unit being adapted for evaluating a signal strength of the first signal and determining the applied force based on the first signal, and
    a first electromagnetic interference coil being adapted for measuring electromagnetic fields,
    wherein a longitudinal axis of the first magnetic field detector unit is arranged such that a first lateral offset between the longitudinal axis of the first magnetic field detector unit and a central axis of the first flux concentrator is provided,
    wherein the first lateral offset is perpendicular to a longitudinal direction of the first flux concentrator,
    wherein the first magnetic field generating unit is formed as a second coil and wound around the first flux concentrator,
    wherein the first flux concentrator includes a first pole and a second pole being arranged with respect to each other in a longitudinal direction of the first flux concentrator, and
    wherein the first magnetic field detector is arranged between the first pole and the second pole,
    wherein the first electromagnetic interference coil is arranged opposite to the first magnetic field detector unit with respect to the first flux concentrator, such that the first electromagnetic interference coil is adapted to detect electromagnetic fields in the surroundings of the first sensing unit and
    wherein the first electromagnetic interference coil is connected to the evaluation unit and is adapted to provide a signal based on which the evaluation unit compensates the effect of interference fields to the first signal.

2. The force measurement sensor according to claim 1, wherein the first lateral offset is perpendicular to the facing orientation of the flux concentrator pointing towards a surface of the object.

3. The force measurement sensor according to claim 1, wherein the longitudinal axis of the first magnetic field detector unit is parallel to a central axis of the first flux concentrator, which central axis is defined by a symmetry axis between the first pole and the second pole of the first flux concentrator.

4. The force measurement sensor according to claim 1, comprising:
    a first feedback element being connected to the evaluation unit and being adapted to provide a comparative signal, based on which the evaluation unit compensates a varying distance between the force measurement sensor and the object.

5. The force measurement sensor according to claim 1, further comprising:
    a second sensing unit including (a) a second flux concentrator having a second facing orientation pointing towards the surface of the object; (b) a second magnetic field generating unit being adapted for generating a magnetic field; (c) a second magnetic field detector unit being adapted for detecting a second magnetic field which field being generated by the second magnetic field generating unit and being influenced by the applied force to be measured,
    wherein the second magnetic field detector unit is further adapted for outputting a second signal being representative for the detected magnetic field,
    wherein a longitudinal axis of the second magnetic field detector unit is arranged such that a second lateral offset between the longitudinal axis of the second magnetic field detector unit and a central axis of the second flux concentrator is provided,
    wherein the second lateral offset is perpendicular to a longitudinal direction of the second flux concentrator, and
    wherein the evaluating unit is adapted for evaluating a signal strength of the first signal and the second signal as to determine the applied force based on both the first signal and the second signal.

6. The force measurement sensor according to claim 5, wherein the second sensing unit is arranged such that the first facing orientation and the second facing orientation intersect under an angle unequal to 0°.

7. The force measurement sensor according to claim 5, wherein the first sensing unit is arranged opposite to the second sensing unit such that the first facing orientation and the second facing orientation are opposed to each other and the angle between the first facing orientation and the second facing orientation is 180°.

8. The force measurement sensor according to claim 5, wherein the evaluation unit is adapted to add the second signal to the first signal and to determine the applied force based on the sum of the first signal and the second signal.

9. The force measurement sensor according to claim 5, wherein the first lateral offset projects from the first flux concentrator in a clockwise direction with respect to the central axis of the first flux concentrator and wherein the second lateral offset projects from the second flux concentrator in a clockwise direction with respect to the central axis of the second flux concentrator.

10. The force measurement sensor according to claim 5, wherein one of the first lateral offset and the second lateral offset projects from the first or second flux concentrator, respectively, in a clockwise direction with respect to the central axis of the first or second flux concentrator, respectively and wherein the other one of the first lateral offset and the second lateral offset projects from the first or second flux concentrator, respectively, in a counterclockwise direction with respect to the central axis of the first or second flux concentrator, respectively.

11. A force measurement arrangement for measuring an applied force onto an object, comprising:
a first sensing unit including (a) a first flux concentrator having a first facing orientation pointing towards a surface of the object; (b) a first magnetic field generating unit being adapted for generating a magnetic field; (c) a first magnetic field detector unit being adapted for detecting a first magnetic field which field being generated by the first magnetic field generating unit and being influenced by the applied force to be measured, wherein the first magnetic field detector unit is further adapted for outputting a first signal being representative for the detected magnetic field; and (d) an evaluating unit being adapted for evaluating a signal strength of the first signal and determining the applied force based on the first signal, and
a first electromagnetic interference coil being adapted for measuring electromagnetic fields,
wherein a longitudinal axis of the first magnetic field detector unit is arranged such that a first lateral offset between the longitudinal axis of the first magnetic field detector unit and a central axis of the first flux concentrator is provided,
wherein the first lateral offset is perpendicular to a longitudinal direction of the first flux concentrator,
wherein the first magnetic field generating unit is formed as a second coil and wound around the first flux concentrator,
wherein the first flux concentrator includes a first pole and a second pole being arranged with respect to each other in a longitudinal direction of the first flux concentrator, and
wherein the first magnetic field detector is arranged between the first pole and the second pole,
wherein the first electromagnetic interference coil is arranged opposite to the first magnetic field detector unit with respect to the first flux concentrator, such that the first electromagnetic interference coil is adapted to detect electromagnetic fields in the surroundings of the first sensing unit and
wherein the first electromagnetic interference coil is connected to the evaluation unit and is adapted to provide a signal based on which the evaluation unit compensates the effect of interference fields to the first signal, and
wherein the object to be measured has a longitudinal axis, the longitudinal axis of the object is parallel to the longitudinal direction of the first flux concentrator.

12. The force measurement arrangement according to claim 11, wherein the object is a rotating shaft.

13. The force measurement arrangement according to claim 11, wherein the first lateral offset is perpendicular to the facing orientation of the flux concentrator pointing towards a surface of the object.

14. The force measurement arrangement according to claim 11, wherein the longitudinal axis of the first magnetic field detector unit is parallel to a central axis of the first flux concentrator, which central axis is defined by a symmetry axis between the first pole and the second pole of the first flux concentrator.

15. The force measurement arrangement according to claim 11, comprising:
a first feedback element being connected to the evaluation unit and being adapted to provide a comparative signal, based on which the evaluation unit compensates a varying distance between the force measurement sensor and the object.

16. The force measurement arrangement according to claim 11, further comprising:
a second sensing unit including (a) a second flux concentrator having a second facing orientation pointing towards the surface of the object; (b) a second magnetic field generating unit being adapted for generating a magnetic field; (c) a second magnetic field detector unit being adapted for detecting a second magnetic field which field being generated by the second magnetic field generating unit and being influenced by the applied force to be measured,
wherein the second magnetic field detector unit is further adapted for outputting a second signal being representative for the detected magnetic field,
wherein a longitudinal axis of the second magnetic field detector unit is arranged such that a second lateral offset between the longitudinal axis of the second magnetic field detector unit and a central axis of the second flux concentrator is provided,
wherein the second lateral offset is perpendicular to a longitudinal direction of the second flux concentrator, and
wherein the evaluating unit is adapted for evaluating a signal strength of the first signal and the second signal as to determine the applied force based on both the first signal and the second signal.

17. The force measurement arrangement according to claim 16, wherein the second sensing unit is arranged such that the first facing orientation and the second facing orientation intersect under an angle unequal to 0°.

18. The force measurement arrangement according to claim 16, wherein the first sensing unit is arranged opposite to the second sensing unit such that the first facing orientation and the second facing orientation are opposed to each other and the angle between the first facing orientation and the second facing orientation is 180°.

* * * * *